(12) United States Patent
Winkler et al.

(10) Patent No.: US 11,432,881 B2
(45) Date of Patent: Sep. 6, 2022

(54) IMAGE MARKER-BASED NAVIGATION USING A TRACKING FRAME

(71) Applicant: Brainlab AG, Munich (DE)

(72) Inventors: Ulrike Winkler, Munich (DE); Robert Essenreiter, Munich (DE); Stefan Hofberger, Munich (DE)

(73) Assignee: Brainlab AG, Munich (DE)

( * ) Notice: Subject to any disclaimer, the term of this patent is extended or adjusted under 35 U.S.C. 154(b) by 142 days.

(21) Appl. No.: 16/316,447

(22) PCT Filed: Aug. 1, 2017

(86) PCT No.: PCT/EP2017/069454
§ 371 (c)(1),
(2) Date: Jan. 9, 2019

(87) PCT Pub. No.: WO2019/024989
PCT Pub. Date: Feb. 7, 2019

(65) Prior Publication Data
US 2020/0337780 A1    Oct. 29, 2020

(51) Int. Cl.
*A61B 34/20* (2016.01)
*A61B 90/00* (2016.01)

(52) U.S. Cl.
CPC ............... *A61B 34/20* (2016.02); *A61B 90/39* (2016.02); *A61B 2034/2055* (2016.02); *A61B 2034/2065* (2016.02); *A61B 2090/3966* (2016.02); *A61B 2090/3983* (2016.02)

(58) Field of Classification Search
None
See application file for complete search history.

(56) References Cited

U.S. PATENT DOCUMENTS

| | | | | |
|---|---|---|---|---|
| 4,706,665 | A | * | 11/1987 | Gouda .................. A61B 90/11 604/116 |
| 6,273,896 | B1 | | 8/2001 | Franck et al. |
| 8,737,708 | B2 | * | 5/2014 | Hartmann ................ G06T 7/73 382/128 |
| 2003/0181918 | A1 | * | 9/2003 | Smothers ............... A61B 6/547 606/86 R |
| 2011/0069867 | A1 | | 3/2011 | Buchner et al. |

(Continued)

FOREIGN PATENT DOCUMENTS

DE    102009034668 A1    1/2011
EP       1 820 465 B1    8/2007
(Continued)

OTHER PUBLICATIONS

Lee et al. "Broken Mayfield Head Clamp" J Korean Neurosurgical Society 45 : 306-308, 2009 (Year: 2009).*

(Continued)

*Primary Examiner* — Luther Behringer
(74) *Attorney, Agent, or Firm* — Tucker Ellis LLP

(57) ABSTRACT

Disclosed is a computer-implemented method for navigating an anatomical body part, a corresponding computer program, a non-transitory program storage medium storing such a program and a computer for executing the program, as well as a system for navigating the anatomical body part, the system comprising an electronic data storage device and the aforementioned computer, and to a system for conducting medical navigation.

18 Claims, 11 Drawing Sheets

(56) References Cited

U.S. PATENT DOCUMENTS

| | | |
|---|---|---|
| 2012/0201421 A1* | 8/2012 | Hartmann ............ A61B 6/5235 |
| | | 382/103 |
| 2014/0126767 A1 | 5/2014 | Daon et al. |
| 2015/0031985 A1 | 1/2015 | Reddy et al. |
| 2016/0106338 A1 | 4/2016 | Kruger |
| 2016/0106508 A1* | 4/2016 | Lathrop ................ A61B 90/39 |
| | | 606/130 |
| 2016/0278875 A1 | 9/2016 | Crawford et al. |

FOREIGN PATENT DOCUMENTS

| | | |
|---|---|---|
| EP | 2676627 A2 | 12/2013 |
| EP | 3454770 B1 * | 10/2019 ............ A61B 34/20 |

OTHER PUBLICATIONS

De Lorenzo et al. "Intraoperative forces and moments analysis on patient head clamp during awake brain surgery" Medical and Biological Engineering Computation (2013) 51:331-341 (Year: 2013).*

European Search Report and Written Opinion corresponding to PCT/EP2017/069454, dated Apr. 9, 2018, pp. 1-12.

Intention to Grant for related European application No. 17 755 074.6, dated Mar. 20, 2019.

Office Action for related European application No. 17 755 074.6, dated Dec. 20, 2018.

* cited by examiner

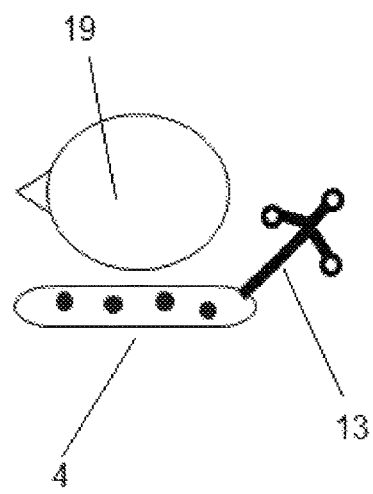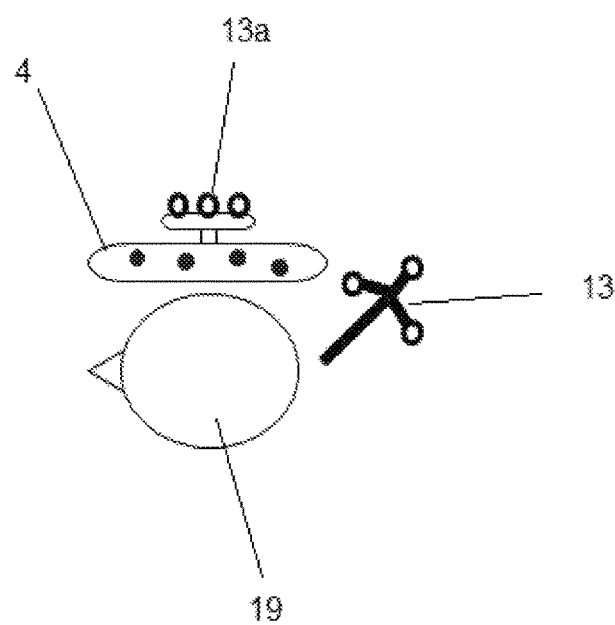
Fig. 1a
(prior art)
Fig. 1b
(prior art)

IMAGE MARKER-BASED NAVIGATION USING A TRACKING FRAME

RELATED APPLICATION DATA

This application is a National Phase Application of International Application No. PCT/EP2017/069454 filed Aug. 1, 2017 and published in the English language.

The present invention relates to a computer-implemented method for navigating an anatomical body part, a corresponding computer program, a non-transitory program storage medium storing such a program and a computer for executing the program, as well as a system for navigating the anatomical body part, the system comprising an electronic data storage device and the aforementioned computer, and to a system for conducting medical navigation.

TECHNICAL BACKGROUND

Automatic image registration is a straight-forward method to directly correlate image data with patient space in a navigated intraoperative imaging workflow. Therefore, either a registration frame is needed which includes image markers visible in image data.

There are currently two approaches of how the step of automatic registration can be performed:

First approach: The registration frame 4 has by construction a known relation to the tracking frame 13 (as shown in FIG. 1*a*). The tracking frame 13 is fixed to the registration frame 4 and there is no flexibility in positioning the tracking frame 4. Second approach: An additional tracking frame 13*a* with a known relation to the registration frame 4 is used (see FIG. 1*b*). The tracking frame 13 can be positioned variably as the additional tracking frame 13*a* is fixed to the registration frame 4. However, an extra transformation step between the additional tracking frame 13*a* and the actual tracking frame 13 has to be done.

If the registration frame has by construction a known relation to the tracking frame, the operation room setup and patient positioning is very limited. If an additional tracking frame is used, the registration accuracy suffers due to an extra coordinate transformation step that is needed. In addition there are setup problems such as visibility of the tracking frames.

Pre-calibrated methods suffer from the need to perform and maintain calibrations that can deteriorate by time. This depends on the hardware of the used scanner and the need to put a permanent tracking frame on the scanner. Maintenance of the scanner, e.g. removing covers where the tracking frame is mounted, or wear of the covers require re-calibrations.

The present invention is designed to provide an improved method for automatic image registration.

The present invention can be used in connection with navigation applications produced by Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE PRESENT INVENTION

In the following, a short description of the specific features of the present invention is given which shall not be understood to limit the invention only to the features or a combination of the features described in this section.

The disclosed method encompasses imaging a patient's anatomical body part, a registration frame containing image markers and a tracking frame containing at least one image marker which is attached to the registration frame. The thus obtained image showing all three aforementioned entities allows determining the spatial relationship between the anatomical body part, the registration frame and the tracking frame. The tracking frame additionally comprises optical markers for navigating a medical procedure, and a registration between the optical markers and the anatomical body part is established on the basis of the aforementioned spatial relationship in conjunction with construction data of the tracking frame containing information about the spatial relationship between the optical markers and the at least one image marker contained in the tracking frame. A system comprising the registration frame and the tracking frame is also disclosed.

GENERAL DESCRIPTION OF THE PRESENT INVENTION

In this section, a description of the general features of the present invention is given for example by referring to possible embodiments of the invention.

In general, the invention reaches the aforementioned object by providing, in a first aspect, a computer-implemented medical data processing method for navigating an anatomical body part. The method comprises executing, on at least one processor of at least one computer (for example at least one computer being part of the navigation system), the following exemplary steps which are executed by the at least one processor.

In a (for example first) exemplary step, planning image data is acquired which depicts (i.e. defines an image, for example a planning image, of) an anatomical body part (such as at least part of the head or of an extremity) supported by a patient support device (such as a head rest or a support device for an extremity) and at least three image markers provided in or on a registration frame attached to the patient support device. The planning image data describes a frame-patient-transformation defining a relative position between the at least three image markers on the one hand and the anatomical body part on the other hand. The image markers are arranged in or on the registration frame for example in a predetermined (e.g. at least one of known or fixed) unsymmetric pattern, for example three-dimensionally unsymmetric three-dimensional pattern, to allow determination of the orientation of the registration frame in the planning image. The planning image data further describes a tracking-registration-transformation defining a relative position between an (for example, at least one, for example exactly one, in a further example at least or exactly three) image marker provided in or on a tracking frame which is directly or indirectly (e.g. via a further unit or device, such as a connector) connected to the registration frame on the one hand and the image markers provided in or on the registration frame on the other hand.

Within the meaning of this disclosure, a transformation is understood to be for example a mapping such as a linear transformation between positions and/or coordinate systems which can be expressed for example as a matrix multiplication.

The planning image data is for example two- or three-dimensional image data (for example, it is tomographic image data). For example, the planning image data has been generated by applying a computed x-ray tomography or magnetic resonance tomography imaging modality to the anatomical body part and the patient support device and the registration frame and the tracking frame, for example by applying the respective imaging modality to the anatomical body part and the patient support device and the registration frame in a state in which it is attached to the patient support device and the tracking frame in a state in which it is connected to the registration frame simultaneously so that the planning image data depicts the anatomical body part and the image markers of the registration frame. It is not necessary that the planning image data depicts the patient support device, which also is generally not the case because the patient support device is normally designed to be at least substantially transparent for the relevant imaging modalities.

The image markers are for example radio-opaque structures (such as spheres containing a material at least partly made from at least one of the substances contained in the group consisting of barium, bismuth, tungsten, gold, titanium, iridium, platinum or rhenium, or for example made from a polymer in combination with one of the aforementioned substances, or at least partly made of a ceramic) or nuclear-magnetically resonant structure (such as fat-water filled spheres) embedded in a comparably less radio-opaque part of the tracking frame and the registration frame, respectively.

The tracking frame is an embodiment of a marker device, for example it is a reference star bearing at least three (for example, exactly three or exactly four) optical markers, and the aforementioned at least one image marker. The tracking frame furthermore comprises a plurality of (for example, at least three, for example exactly three, or at least four, for example exactly four) optical markers in a predetermined (e.g. at least one of known or fixed) spatial relationship (e.g. at least one of position and orientation) relative to the at least one image marker provided in or on the tracking frame.

In one example, the tracking frame includes a tracking marker array including the at least three optical markers and a tracking frame connector which is connected to both the tracking marker array and the registration frame. The image marker provided in or on the tracking frame may be provided for example in or on the tracking frame connector. In one variation of this example, the tracking marker array and the tracking frame connector are provided as a single piece (i.e. in one piece) or as separate connectable and/or connected pieces.

In one example, the tracking frame is attached to the registration frame at a predetermined position on the registration frame (for example, one of a plurality of, e.g. exactly four, fixed positions on the registration frame for attaching the tracking frame to the registration frame). For example, the registration frame is provided with a plurality of such as at least two [for example, exactly four] attachment parts for attaching the tracking frame (for example in a predetermined orientation relative to the registration frame) or, as far as the method includes using the tracking frame connector, the tracking frame connector (for example in a predetermined orientation relative to the registration frame). For example, the location of the predetermined position is determined (as part of the method according to the first aspect) based on the tracking-registration-transformation and the relative position between the image markers provided in or on the registration frame is determined based on the location of the predetermined position and the construction data, for example based on the tracking frame transformation.

In one example of the disclosed method, the image markers are or have been imaged using a first imaging modality (for example, a three-dimensional imaging modality such as a tomographic imaging modality such as computed x-ray tomography or magnetic resonance tomography or a sonography or a two-dimensional imaging modality such as fluoroscopy). For example, the optical markers are or have been detected using a navigation modality (such as infrared or electromagnetic tracking), wherein the navigation modality operates in an electromagnetic wavelength band different, for example disjunct, from the wavelength band in which the imaging modality operates.

In a (for example second) exemplary step, construction data (available for example from computer-aided design of the tracking frame) is acquired which describes a predetermined tracking frame-transformation defining a relative position between at least three optical markers and the image marker provided in or on the tracking frame.

In a (for example third) exemplary step, a registration of the anatomical body part is determined as a relative position between the optical markers and the depiction of the anatomical body part by the planning image data. The registration is determined based on the frame-patient-transformation and by determining the relative position between the image markers provided in or on the registration frame on the one hand and the optical markers on the other hand based on the tracking-registration-transformation and the tracking frame-transformation. The registration constitutes for example a definition of a spatial relationship between the optical markers and the depiction of the anatomical body part (the position of the anatomical part being defined in the coordinate space of the planning image data, i.e. a planning reference system), and being related to the position of the optical markers which is defined in the coordinate space in which navigation is conducted (i.e. a navigation reference system) via a transformation defined by e.g. the frame-patient transformation and the tracking-registration-transformation and the tracking frame-transformation. That spatial relationship may be stored for further use during e.g. a navigated medical procedure.

In one example, the frame-patient-transformation is defined in the planning reference system. In that case, for example, marker navigation data is acquired which describes a position of the optical markers in the navigation reference system, and the position of the anatomical body part is transformed between a planning reference system in which positions in the planning image data are defined and the navigation reference system using a reference system transformation (i.e. a transformation between the reference systems, namely between the navigation reference system and the planning reference system). For example, the position of the anatomical body part is transformed from the planning reference system into the navigation reference system using the reference system transformation.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect.

In a third aspect, the invention is directed to a non-transitory computer-readable program storage medium on which the program according to the fourth aspect is stored.

In a fourth aspect, the invention is directed to at least one computer (for example, a computer), comprising at least one processor (for example, a processor) and at least one memory (for example, a memory), wherein the program according to the fourth aspect is running on the processor or is loaded into the memory, or wherein the at least one computer comprises the computer-readable program storage medium according to the fifth aspect.

In a fifth aspect, the invention is directed to a system for conducting medical navigation, the system according to the fifth aspect comprising:
- a) a tracking frame (such as the above-described tracking frame) including at least one image marker and at least three optical markers, for example including a tracking marker array comprising the three optical markers; and
- b) a registration frame (such as the above-described registration frame), comprising:
  a patient support unit attachment portion for attaching the registration frame to a patient support unit (such as a the above-described patient support unit);
  at least three image markers which are arranged, for example in a three-dimensional unsymmetric pattern, in or on the registration frame; and
  at least one (for example, a plurality of, e.g. four or exactly four) attachment part for attaching the tracking frame directly (i.e. without any separate intermediate part) or indirectly (i.e. via a tracking frame connector) to the registration frame.

The system according to the fifth aspect is suitable for use within execution of the method according to the first aspect.

In one example of the system according to the fifth aspect, the tracking frame comprises a tracking marker array comprising the three optical markers and a tracking frame connector for connecting the tracking marker array with the registration frame, wherein the at least one image marker provided in or on the tracking frame is provided in or on the tracking frame connector. In one variation of this example, the tracking marker array and the tracking frame connector are provided as a single piece (i.e. in one piece) or as separate connectable and/or connected pieces. Having the two parts as separate pieces provides the advantage that only the tracking frame connector needs to be imaged for generation of the planning image data and that the tracking marker array does not need to be attached to the registration frame during the imaging procedure because the tracking marker array may be damaged or otherwise hamper the imaging procedure.

In one example of the system according to the fifth aspect, the attachment part is constituted such that the tracking frame is attachable to the registration frame in a predetermined orientation relative to the registration frame.

In one example of the system according to the fifth aspect, at least two (for example, exactly two, three or exactly three) image markers are provided in or on the tracking frame (if applicable, for example in or on the tracking frame connector), and wherein the attachment part is constituted such that the tracking frame is attachable to the registration frame in a not-predetermined orientation relative to the registration frame.

In a sixth aspect, the invention is directed to a system for navigating an anatomical body part, the system according to the sixth aspect comprising:
- a) the at least one computer according to the fourth aspect;
- b) at least one electronic data storage device storing at least the planning image data and the construction data; and
- c) the system according to the fifth aspect; and
- d) a tracking device (for example, a stereoscopic camera operating in the infrared wavelength band) for tracking the position of the optical markers,
  wherein the at least one computer is operably coupled to
  the at least one electronic data storage device for acquiring, from the at least one data storage device, at least the planning image data and the construction data, and
  to the tracking device for acquiring, from the tracking device, signals corresponding to information about the positions of the optical markers.

In general, the invention does not involve or for example comprise or encompass an invasive step which would represent a substantial physical interference with the body requiring professional medical expertise to be carried out and entailing a substantial health risk even when carried out with the required professional care and expertise. For example, the invention does not comprise a step of irradiating the anatomical body part and/or the patient's body with ionizing radiation so that it does not comprise any steps of therapy of the human or animal body, for example it does not comprise any step of radiotherapy or radiosurgery. More particularly, the invention does not involve or in particular comprise or encompass any surgical or therapeutic activity. The invention is instead directed as applicable to registering a patient placed ready for a medical procedure to a planning image for example before any therapeutic or surgical activity ensues. For this reason alone, no surgical or therapeutic activity and in particular no surgical or therapeutic step is necessitated or implied by carrying out the invention.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

A navigation system for computer-assisted surgery preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

DESCRIPTION OF THE FIGURES

In the following, the invention is described with reference to the appended figures which give background explanations and represent specific embodiments of the invention. The scope of the invention is however not limited to the specific features disclosed in the context of the figures, wherein FIGS. 1a and 1b illustrate the two approaches to automatic image registration known from the state of the art;

FIGS. 14a to 16 illustrate perspective views of the tracking frame connector;

FIG. 1a illustrates the first prior art approach discussed above, and FIG. 1b discusses the second prior art approach discussed above.

FIG. 2 is a flow diagram illustrating the basic steps of the disclosed method in accordance with the first aspect, which in the illustrative example of FIG. 1 starts with a step S11 of acquiring the planning image data. In subsequent step S12, the construction data is acquired, followed by step S13 which encompasses determining the registration between the anatomical body part in the planning image and the optical markers.

FIGS. 3 to 8 illustrate the system according to the fifth aspect from multiple perspectives. Throughout the figures, same reference signs denote the same parts. The system 1 is suitable for conducting medical navigation and comprises a tracking frame 13 and a registration frame 4. In the example of FIGS. 3 to 8, two tracking frames 13 are shown as being attached or attachable to the registration frame 4, even though the method according to the first aspect requires only one tracking frame 13 to be executed. The tracking frame 13 includes at least one tracking frame image marker 11 and four optical markers 3 arranged on the arms of reference star embodying a tracking marker array 2. The registration frame 4 comprises a patient support unit attachment portion 9 for attaching the registration frame 4 to a patient support unit (e.g. to a headrest). The patient support unit attachment portion 9 may take the form of a throughhole formed perpendicular to a surface of a central base part 14 of the registration frame 4.

Figures 14A, 14B, 14C:
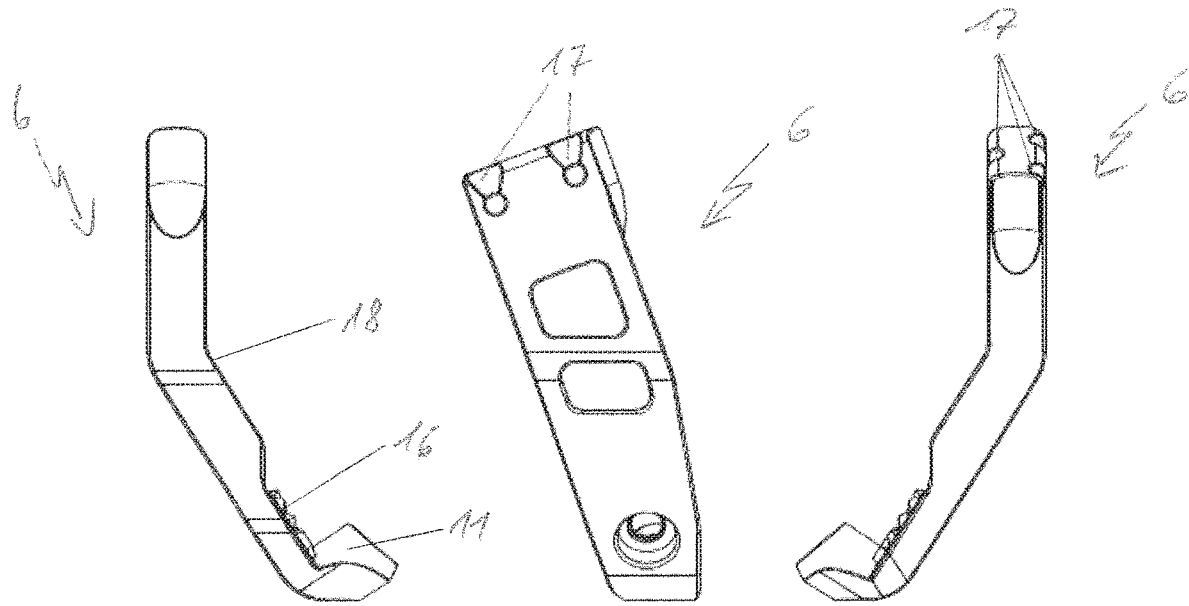
Figures 15A, 15B:
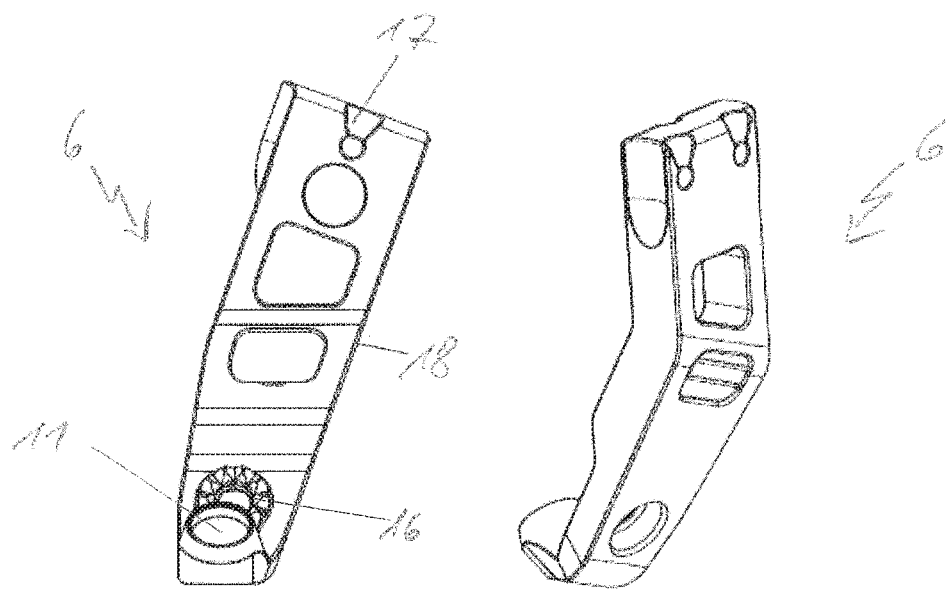
Figure 16:
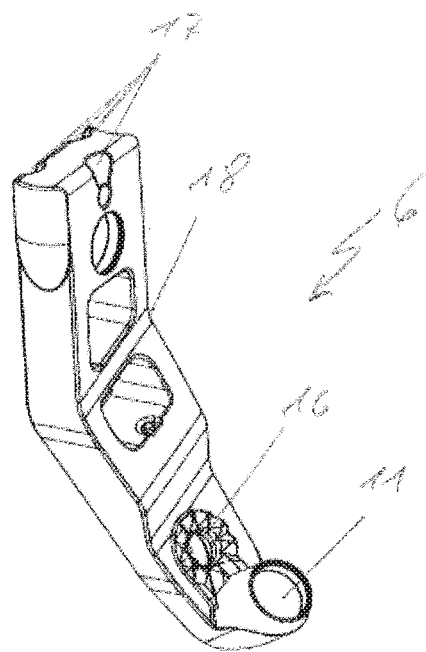

The tracking frame 13 is coupled to the registration frame 4 via a tracking frame connector 6 which is illustrated in further detail in FIGS. 14 to 16. The tracking frame connector 6 comprises an articulated base part 18 having a throughhole 16 at its lower end for feeding through a screw 7 for attaching the tracking frame connector 6 to an attachment part 5 formed in the registration frame 4 for attaching the tracking frame 13 to the registration frame 4. The attachment part 5 and the throughhole 16 are each provided with a toothed circumference comprising interlocking teeth so that a stable positioning of the tracking frame 13 to the registration frame 4 is supported. The tracking frame image marker 11 at the lower end of the tracking frame 13 or the tracking frame connector 6, respectively, is enclosed in a housing (which in the embodiment shown in the figures may for example be circular) protruding from the side of the tracking frame 13 or the tracking frame connector 6, respectively, which, when attached to the registration frame 4, faces the registration frame 4. At its upper end, the tracking frame connector 6 comprises three locks for interlocking with the tracking marker array (for example, a suitably adapted base part of the tracking marker array 2).

Figure 2:
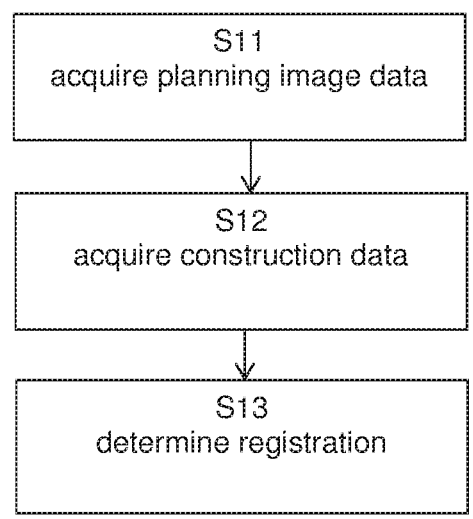
FIG. 2 shows a basic flow of the method according to the first aspect.
Figure 3:
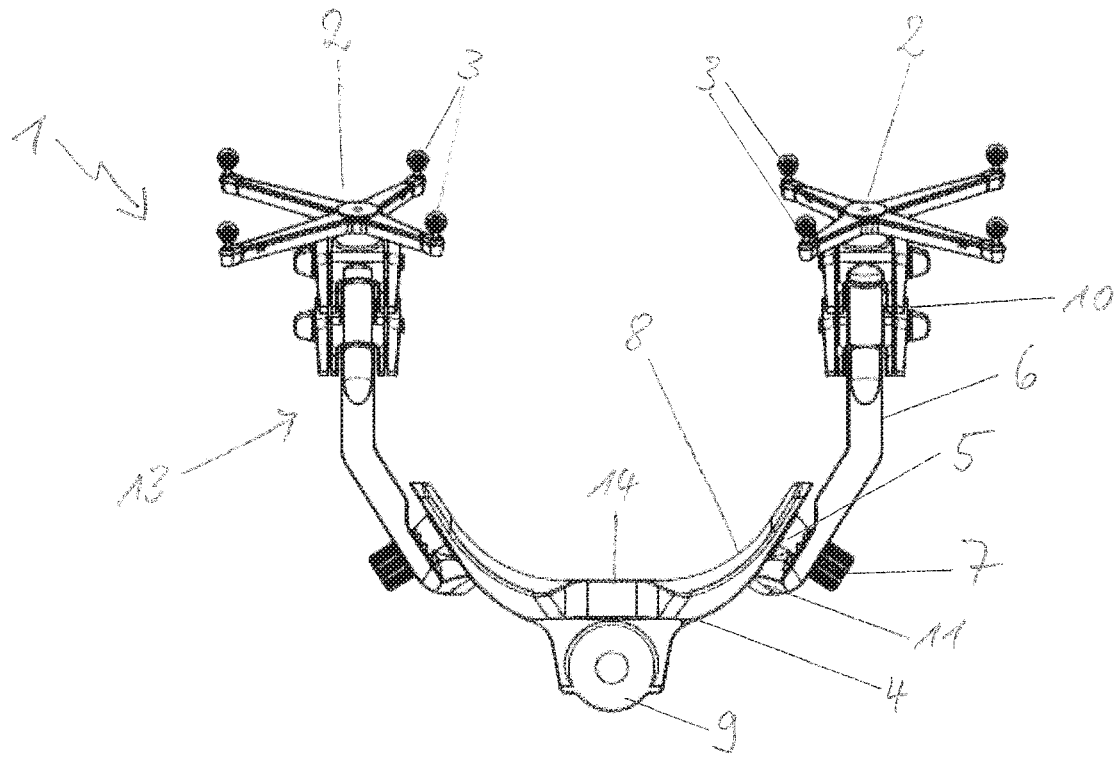
FIGS. 3 to 8 illustrate perspective views of the system according to the fifth aspect.
Figure 4:
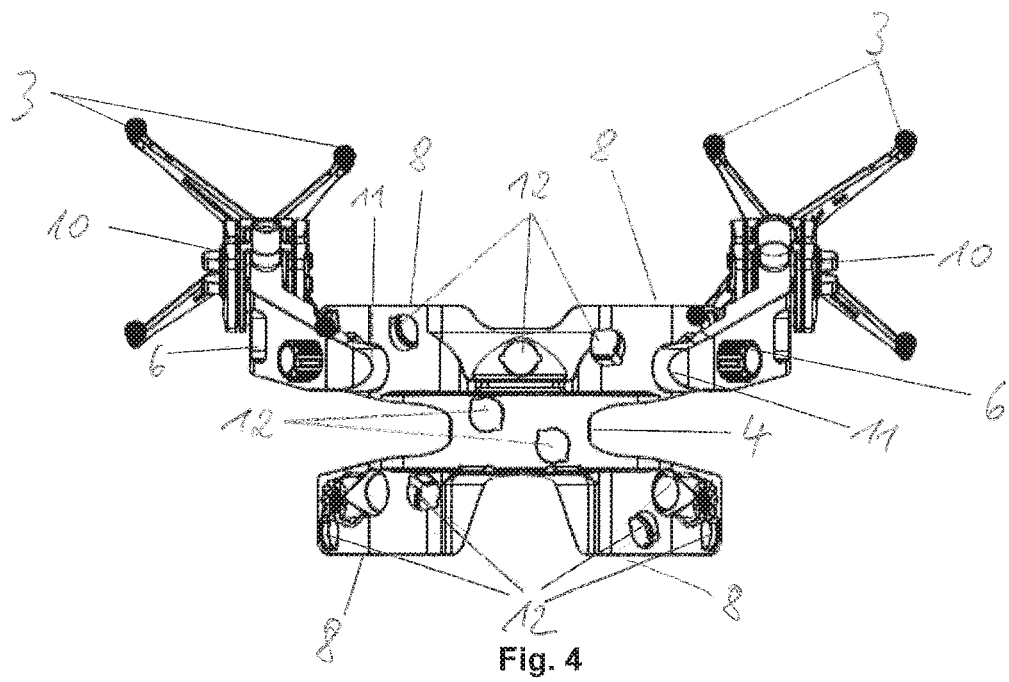
Figure 5:
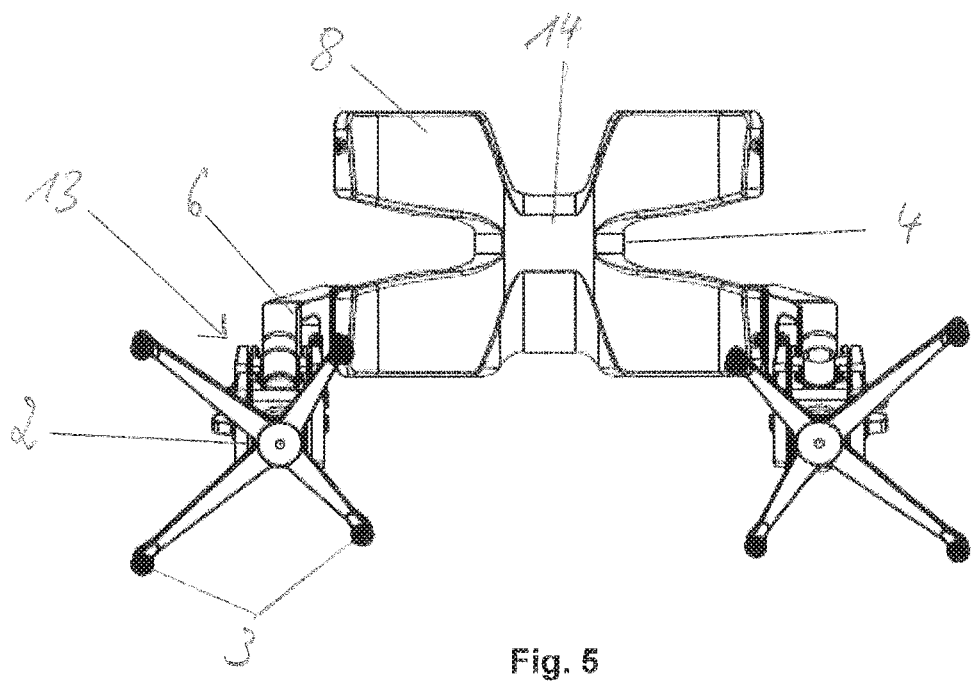
Figure 6:
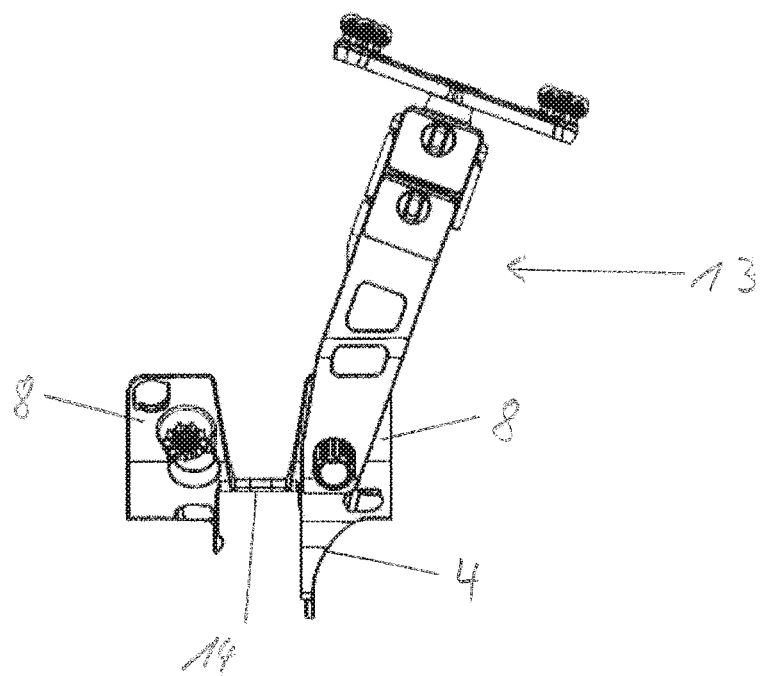
Figure 7:
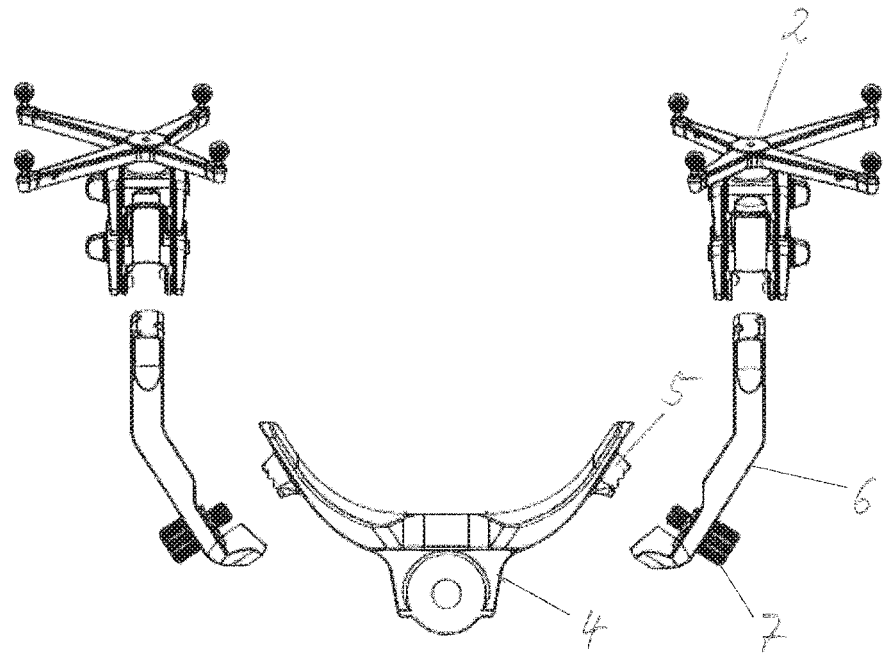
Figure 8:
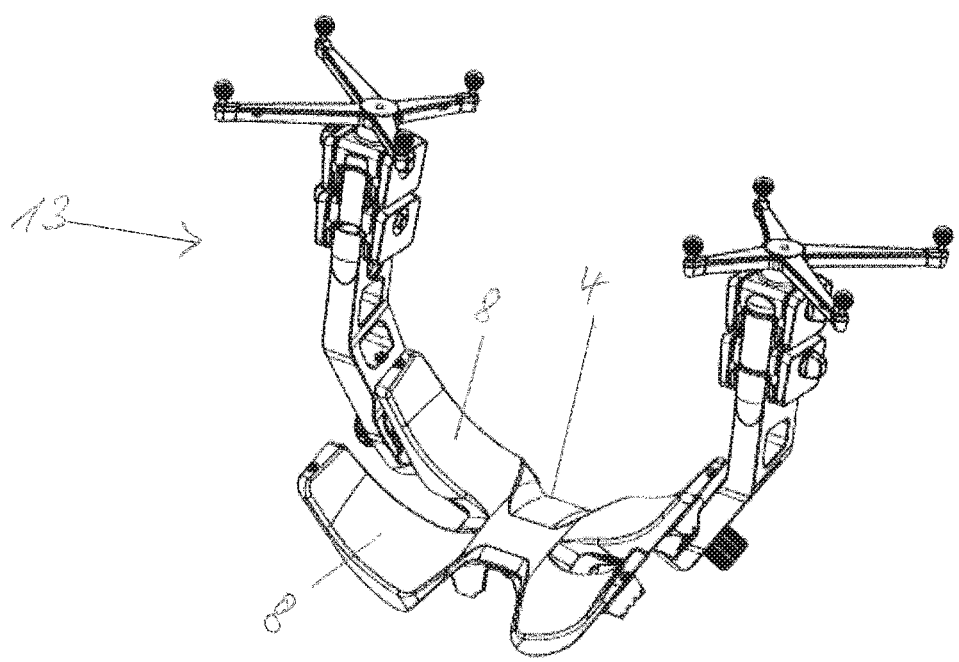
Figure 9:
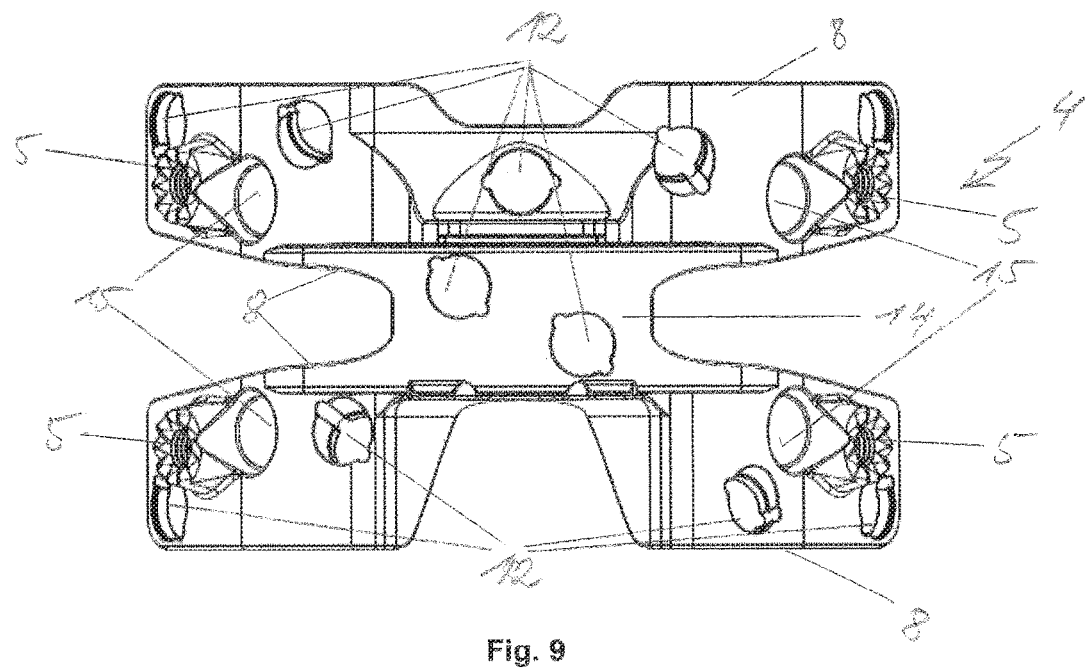
FIGS. 9 to 13 illustrate perspective views of the registration frame.
Figure 10:
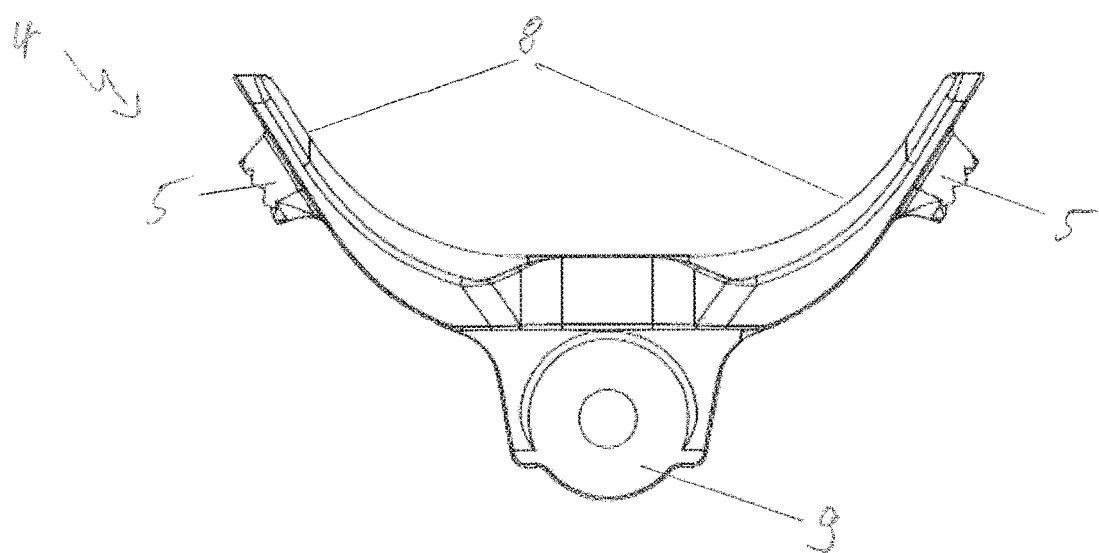
Figure 11:
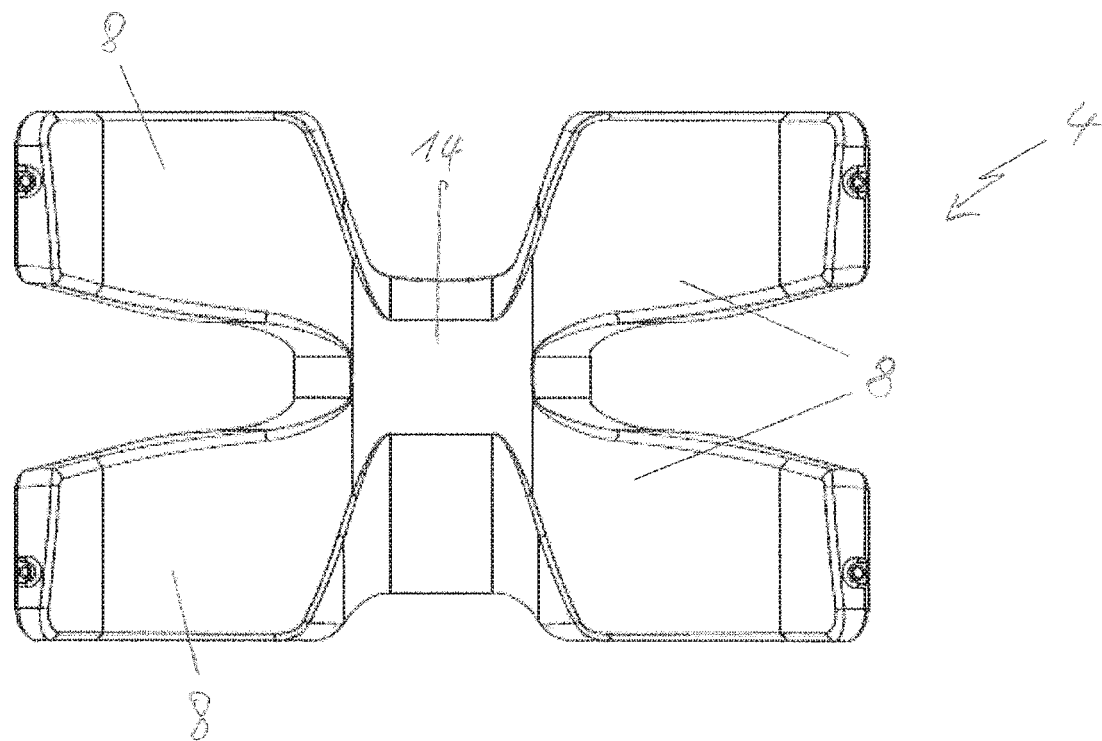
Figure 12:
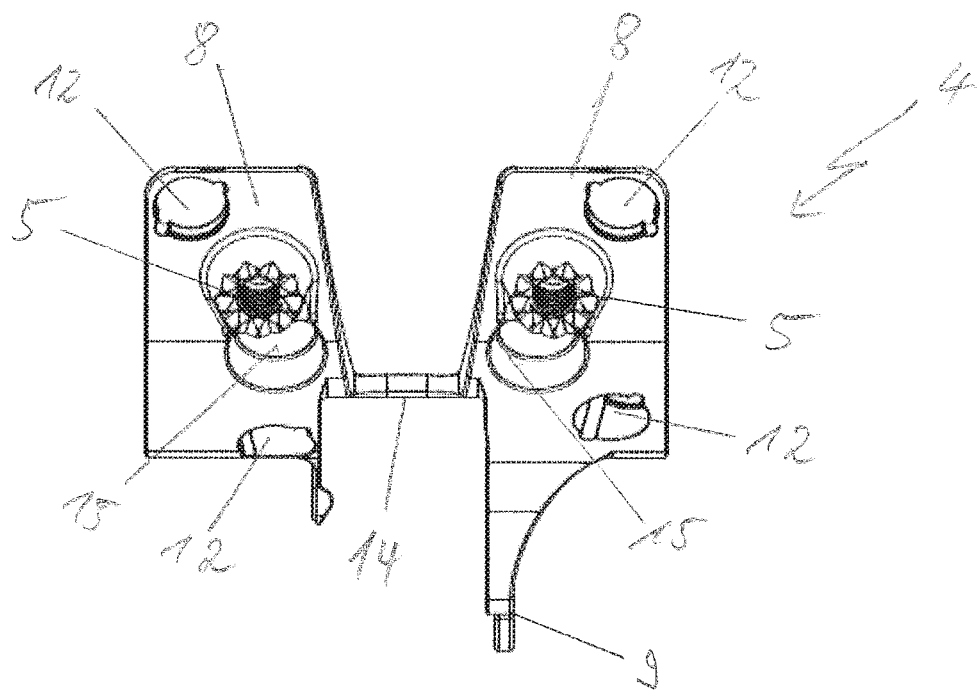
Figure 13:
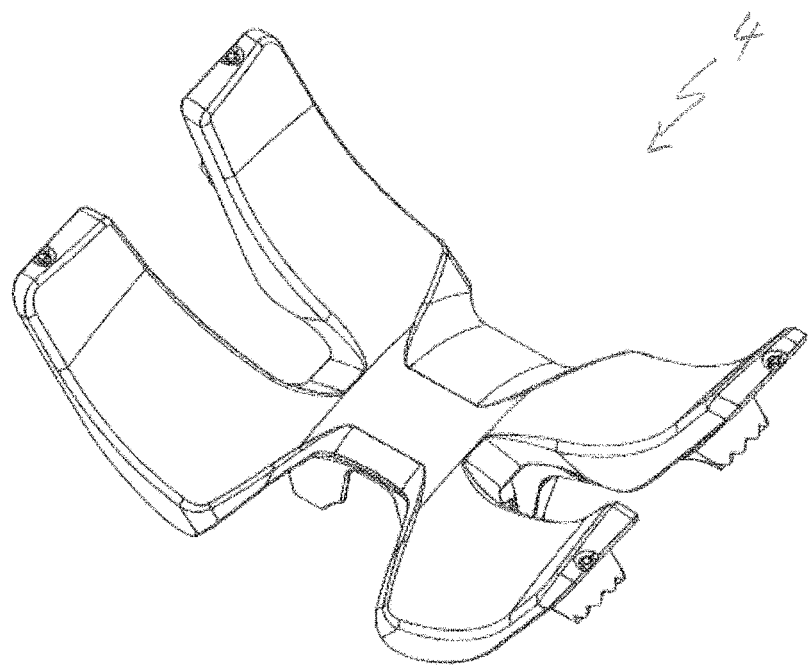

As may be seen from the bottom view of the system 1 illustrated in FIG. 4, the registration frame 4 comprises a total of eleven registration frame image markers 12 in the interior of the material forming the registration frame 4 which are distributed along the side arms 8 of and the base part 14 of the registration frame 4 in an unsymmetric manner. Furthermore, the registration frame 4 comprises fixing parts 15 formed as circular recesses in the side arms 8 into which the housing which at least partly encloses the tracking frame image marker 11 of the tracking frame 13 or the tracking frame connector 6, respectively, is inserted when the screw 7 lead through throughhole 16 and the attachment part is tightened. Thereby, the spatial relationship between the tracking frame 13 and the registration frame 4 is fixed and stabilized, and the relative orientation between the tracking frame 13 and the registration frame 4 is a predetermined orientation when the tracking frame 13 or the tracking frame connector 6, respectively, is attached with the registration frame 4. The registration frame 4 is illustrated in more detail in FIGS. 8 to 13, wherein notably FIG. 11 is a top view, FIG. 12 is a side view, FIG. 13 is a perspective view from overhead showing the system 7 of FIG. 8 but with the tracking frame 13 removed, and FIG. 9 is view from below, and FIG. 10 is another side view (end view) of the registration frame from a direction perpendicular to the viewing direction of FIG. 12. As can be seen from the figures, the registration frame 4 comprises a total of four attachment parts 5 and each an associated fixing part 15 (i.e. a total of four fixing parts 15) so that a tracking frame 13 or tracking frame connector 6, respectively, may be attached to the registration frame 4 at each one of the predetermined positions on the registration frame defined by the attachment parts 5 in association with the fixing parts 15.

FIGS. 14a to 16 show different perspectives of the tracking frame connector 6. From those figures, it is clear that the housing of the image marker 11 included in the tracking frame 13 or the tracking frame connector 6, respectively, protrudes from the lower end of the base part 18 of the tracking frame connector 6 in a direction facing towards the registration frame 4 when the tracking frame 13 is attached to the registration frame 4. The housing and the image marker 11 are formed such that the housing (and, for example, the image marker 11) can be located in, i.e. fits into, the fixing parts 15.

Figure 17:
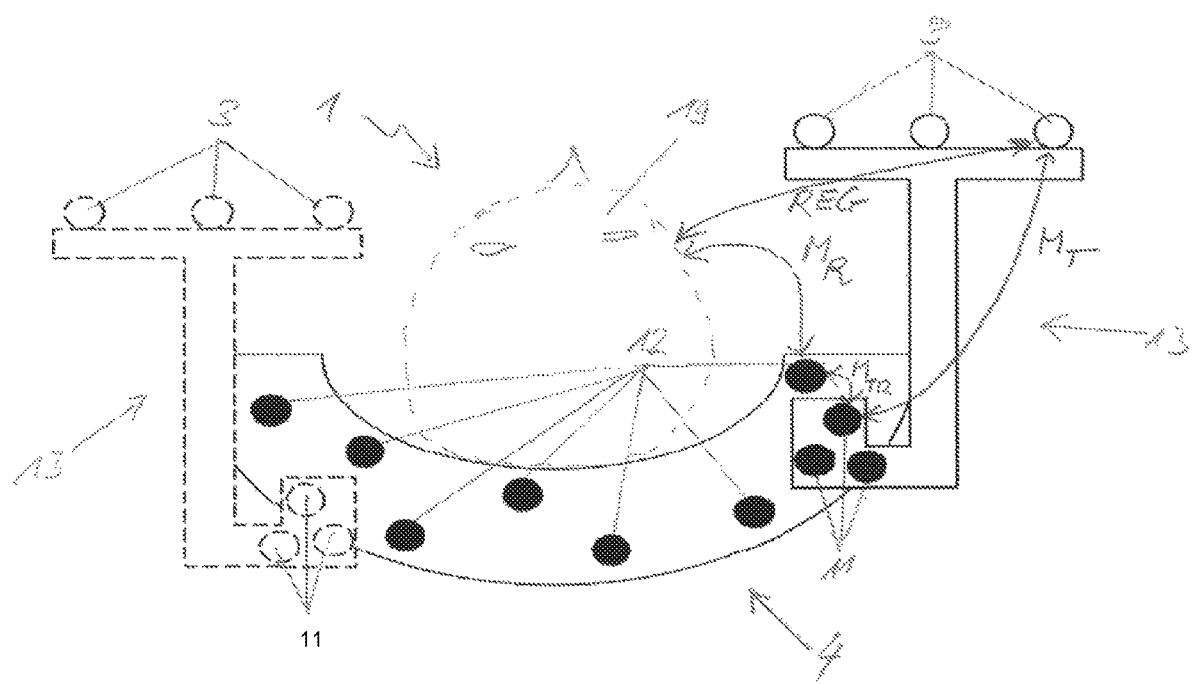
FIG. 17 illustrates use of the system according to the fifth aspect for implementing the method according to the first aspect.

FIG. 17 illustrates use of the system according to the fifth aspect for implementing the method according to the first aspect. An anatomical body part 19 (in this case, the head) of the patient is placed on a patient support unit to which the system 1 is attached. FIG. 17 illustrates use of an optional second tracking frame 13 (shown in dashed lines) in addition to a first tracking frame 13 (shown in solid lines). Each one of the two tracking frames comprises not only image marker 11 but three image markers 11. This allows attaching the tracking frame 13 to the registration frame 4 without having a predetermined orientation of the tracking frame 13 relative to the registration frame 4. The orientation of the tracking frame 13 relative to the registration frame 4 may be determined from the planning image because the geometry of the arrangement of image markers 11 is known and the imaged geometry can be compared to the known geometry in order to determine the orientation.

The method according to the first aspect allows for automatic registration of an image data set (the planning image data) by detecting the registration frame 4 in the image data set and using the tracking frame 13. The registration frame contains the image markers 12 that are detectable in the image data set whereas the tracking frame 13 contains both the image markers 11 that are detectable in the image data set and optical markers 3 (navigation markers) that are visible to an optical, electromagnetic, or other tracking system. The tracking frame connector 6 for connecting the tracking frame 13 to the registration frame 4 includes one or more image markers 11 for detection in the image data set. The tracking frame connector 6 and the tracking marker array 2 could also be one part. The tracking frame connector 6 provides a distinctive interface for the tracking frame 13. The image marker(s) 11 in the tracking frame connector 6 enable the position detection of the tracking frame 13 in the image data set. The number of position markers in the tracking frame connector 6 affects the degrees of freedom the interface between registration frame 4 and tracking frame connector 6 may provide.

The registration REG is the spatial relation of the optical markers 3 to the planning image data. This spatial relation is defined by at least the following three components:

1. The known spatial relation, the tracking frame-transformation $M_T$, of the optical markers 3 and the image markers 11 in the tracking frame.

2. The calculated spatial relation, the tracking-registration-transformation $M_{TR}$, of the image markers 11 in the tracking frame 4 and the image markers 12 in the registration frame 4.

3. The calculated spatial relation, the frame-patient-transformation $M_R$, of the image markers 12 in the registration frame 4 and the image data.

$M_T$ is given by the construction data of the tracking frame 4.

$M_{TR}$ is calculated in the following way:

Image markers are detected by an algorithm executed on the planning image data.

For example, image markers for CT data must comprise a material that has a distinguishable Hounsfield value compared to its surrounding volume, whereas image markers for MR data often contain water that contrasts to the surrounding air.

If the pixel value of an image marker (e.g. for CT the Houndsfield value) is roughly known, the algorithm filters the image data by putting a window of a certain size around this value and removes all image contents outside this window. Ideally only the markers remain in this filtered data set. If this pixel value is not known (as often for MR), the image data have to be searched by a moving window filter to find the correct pixel value.

Knowing the shape and size of an image marker, the algorithm then searches for features in the image data that have that size and shape, removing all other features. This may be done by applying the well-known connected components approach.

In a last optimization step, the remaining features in the image data can be analyzed with respect to their quality of fit: for example for a spherical marker the spherical mismatch can be calculated (i.e. how well the voxels of the markers fill a sphere of a known radius).

The centre of each image marker 11, 12 found in this way is the coordinate of that marker in the image data resulting in a set of detected marker coordinates.

The set of marker coordinates now ideally contains both, the image marker(s) 11 of the tracking frame 13 and the image markers 12 of the registration frame 4. Since the geometry of both the marker(s) 11 of the tracking frame 13 and the markers 12 of the registration frame 4 are known, an optimization algorithm searches all marker coordinates in the image data that have the best fit to the marker coordinates of the tracking frame, as well as to the marker coordinates of the registration frame 4, respectively. This can be done by well-known least squares optimization algorithms.

This eventually results in the mapping of the coordinates of the registration frame 4 to the image data set and the mapping of the coordinates of the tracking frame 13 to the same image data set. Knowing both mappings, the relation of the tracking frame 13 to the registration frame 4 in the image coordinate system (i.e. the relation $M_{TR}$) can be easily calculated by multiplication of the two mapping matrices. The relation $M_R$ is the mapping of the registration frame to the image data coordinate system.

The final image registration is now calculated in one step by chaining all three transformations determined above: $M_T * M_{TR} * M_R$ The number of image markers 12 in the registration frame 4 has to be sufficient to find a unique mapping of the markers to the image data set. The absolute minimum number of image markers 12 here is three.

The number of image markers 11 in the tracking frame 13 depends on the degrees of freedom of the variability of the orientation of the tracking frame 13 with respect to the registration frame 4. If this degree of freedom is one, one image marker 11 is sufficient. The more degrees of freedom, the more image markers 11 are required.

By knowing the spatial relation between the tracking frame 13 and the registration frame 4, the following advantages are achieved:
  no additional tracking frame 13 is required and therefore no further transformation step between tracking frames 13 is needed that possibly decreases accuracy;
  the tracking frame 13 can be mounted to different positions allowing more freedom for the surgery setup, higher accuracy and less visibility problems.

In general the hardware can be manufactured by milling, injection molding or rapid manufacturing technologies like selective laser sintering or likewise. The materials shall be suitable for the respective imaging technology (e.g. MRI, CT). For example, plastics are used which could be fiber-reinforced.

Figure 18:
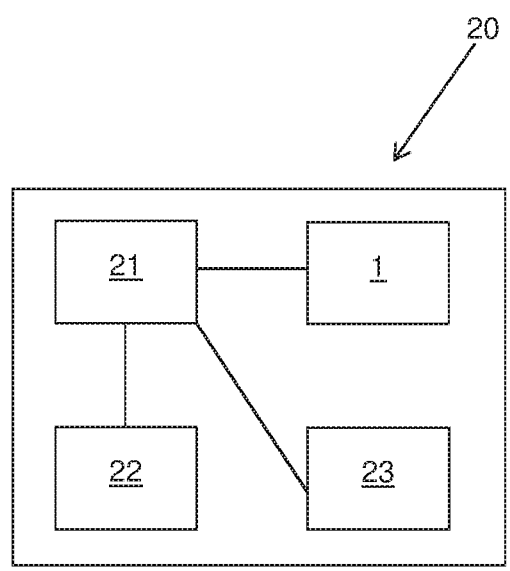
FIG. 18 is a block diagram illustrating the components of the system according to the sixth aspect.

A system 20 according to the sixth aspect for navigating an anatomical body part 19 is schematically illustrated in FIG. 18. The system 20 comprises:
  at least one computer 21 configured to execute a program for implementing the method according to the first aspect;
  at least one electronic data storage device 22 storing at least the planning image data and the construction data;
  the system 1 according to the fifth aspect; and
  a tracking device 23 for tracking the position of the optical markers 3,
    wherein the at least one computer 21 is operably coupled to
      the at least one electronic data storage device 22 for acquiring, from the at least one data storage device 22, at least the planning image data and the construction data, and
      to the tracking device 23 for acquiring, from the tracking device 23, signals corresponding to information about the positions of the optical markers 3.

The invention claimed is:

1. A system for conducting medical navigation, the system comprising:
  a registration frame; and
  a tracking frame comprising:
    i) a tracking marker array comprising at least three optical markers;
    ii) a tracking frame connector for connecting the tracking frame with the registration frame; and
    iii) a tracking frame image marker provided in or on the tracking frame connector,
  wherein the registration frame comprises:
    a patient support unit attachment portion for attaching the registration frame with a patient support unit;
    at least three registration frame image markers arranged in or on the registration frame; and
    a plurality of attachment parts for attaching the tracking frame with the registration frame,
  wherein the tracking marker array and the tracking frame connector comprise separate interlockable pieces,
  wherein the tracking frame connector of the tracking frame comprises a base part defining on an end thereof a through hole configured to selectively receive an associated fastener therethrough for fastening the tracking frame with a selected one of the plurality of attachment parts of the registration frame.

2. The system according to claim 1, wherein the plurality of attachment parts are constituted such that the tracking frame is selectively attachable with the registration frame in a selected predetermined orientation relative to the registration frame.

3. The system according to claim 1, further comprising:
  at least three image markers provided in or on the tracking frame,
  wherein the plurality of attachment part are constituted such that the tracking frame is attachable with the registration frame in a selectable orientation relative to the registration frame.

4. The system according to claim 1, wherein:
  the at least three optical markers comprise optical marker structures that are detectable by an associated medical navigation system using a navigation modality of operation of the associated medical navigation system comprising one or more of:
    an infrared tracking of the optical marker structures by the associated medical navigation system; and/or an electromagnetic tracking of the optical marker structures by the associated medical navigation system; and the at least three registration frame image markers and the tracking frame image marker comprise image marker structures that are imageable by application of a three-dimensional imaging modality to the at least three registration frame image markers and the tracking frame image marker.

5. The system according to claim 1, wherein:
the at least three optical markers comprise optical marker structures that are detectable by an associated medical navigation system using a navigation modality of operation of the associated medical navigation system comprising one or more of:
an infrared tracking of the optical marker structures by the associated medical navigation system; and/or
an electromagnetic tracking of the optical marker structures by the associated medical navigation system; and the at least three registration frame image markers and the tracking frame image marker comprise image marker structures that are imageable by application of one or more of:
tomographic imaging;
computed x-ray tomography;
magnetic resonance tomography; and/or
sonography.

6. The system according to claim 1, wherein:
the at least three optical markers comprise optical marker structures that are detectable by an associated medical navigation system using a navigation modality of operation of the associated medical navigation system comprising one or more of:
an infrared tracking of the optical marker structures by the associated medical navigation system; and/or
an electromagnetic tracking of the optical marker structures by the associated medical navigation system; and the at least three registration frame image markers and the tracking frame image marker comprise image marker structures that are imageable by application of a two-dimensional imaging modality.

7. The system according to claim 6, wherein:
the at least three registration frame image markers and the tracking frame image marker comprise image marker structures that are imageable by the associated medical navigation system using fluoroscopy.

8. The system according to claim 1, wherein:
the at least three registration frame image markers and the tracking frame image marker comprise radio-opaque structures or nuclear-magnetically resonant structures.

9. The system according to claim 1, wherein:
the at least three optical markers comprise optical marker structures that are detectable by an associated medical navigation system using a first electromagnetic wavelength band; and
the at least three registration frame image markers and the tracking frame image marker comprise image marker structures that are imageable by application of a second electromagnetic wavelength band different than the first electromagnetic wavelength band.

10. The system according to claim 1, wherein:
the at least three optical markers are detectable by an associated medical navigation system using a navigation modality of operation of the associated medical navigation system;

the at least three registration frame image markers are imageable by application of an imaging modality of operation of an associated medical imaging system; and
the tracking frame image marker is imageable by application of the imaging modality of operation of the associated medical imaging system.

11. The system according to claim 1, wherein:
the through hole on the end of the base part defines a toothed circumference comprising teeth; and
the selected one of the plurality of attachment parts of the registration frame comprises a corresponding toothed circumference comprising teeth configured to interlock with the teeth of the toothed circumference defined by the through hole on the end of the base part when the tracking frame is attached with the registration frame.

12. The system according to claim 1, wherein:
the tracking frame connector of the tracking frame comprises:
a housing protruding from a side of the tracking frame; and
the registration frame comprises:
a central base part;
a plurality of side arms extending from the central base part; and
a plurality of fixing parts comprising recesses defined in the plurality of side arms, wherein the recesses are configured to receive the housing protruding from a side of the tracking frame when the tracking frame is attached with the registration frame.

13. The system according to claim 12, wherein:
the image marker of the tracking frame is disposed in the housing protruding from a side of the tracking frame, whereby the image marker is disposed in the first recess of the plurality of fixing parts adjacent to the selected one of the plurality of attachment parts of the registration frame when the tracking frame is attached with the registration frame.

14. The system according to claim 13, wherein:
the base part of the tracking frame connector is articulated;
the housing protruding from a side of the tracking frame is circular; and
the recesses of the plurality of fixing parts are circular and configured to receive the circular housing protruding from a side of the tracking frame.

15. The system according to claim 13, wherein:
the through hole on the end of the base part defines a toothed circumference comprising teeth; and
the selected one of the plurality of attachment parts of the registration frame comprises a corresponding toothed circumference comprising teeth configured to interlock with the teeth of the toothed circumference defined by the through hole on the end of the base part.

16. The system according to claim 12, wherein:
the plurality of attachment parts of the registration frame are disposed on the a plurality of side arms extending from the central base part.

17. A system for conducting medical navigation, the system comprising:
a registration frame; and
a tracking frame comprising a tracking marker array comprising:
at least three optical markers;
a tracking frame connector for connecting the tracking frame with the registration frame; and
a tracking frame image marker provided in or on the tracking frame connector, wherein the registration frame comprises:
- a patient support unit attachment portion for attaching the registration frame with a patient support unit;
- at least three registration frame image markers arranged in or on the registration frame;
- a plurality of attachment parts for attaching the tracking frame with the registration frame,
- a central base part;
- a plurality of side arms extending from the central base part; and
- a plurality of fixing parts comprising recesses defined in the plurality of side arms, wherein the recesses are configured to receive a housing protruding from a side of the tracking frame when the tracking frame is attached with the registration frame, wherein the tracking marker array and the tracking frame connector comprise separate interlockable pieces.

18. The system according to claim 17, wherein:
the plurality of fixing parts comprise a toothed circumference comprising teeth configured to interlock with the teeth of a toothed circumference defined by the tracking frame connector when the tracking frame is attached with the registration frame.

* * * * *